(12) United States Patent
Chen et al.

(10) Patent No.: US 8,104,468 B2
(45) Date of Patent: Jan. 31, 2012

(54) LARYNGEAL MASK AIRWAY AND CLIP DEVICE

(76) Inventors: Tien-Sheng Chen, Taipei (TW); Hui-Bih Yuan, Taipei (TW)

( * ) Notice: Subject to any disclaimer, the term of this patent is extended or adjusted under 35 U.S.C. 154(b) by 538 days.

(21) Appl. No.: 12/342,176

(22) Filed: Dec. 23, 2008

(65) Prior Publication Data

US 2009/0194113 A1 Aug. 6, 2009

(30) Foreign Application Priority Data

Jan. 31, 2008 (TW) .................. 97103788 A

(51) Int. Cl.
*A62B 18/08* (2006.01)
(52) U.S. Cl. .......... 128/200.26; 128/206.16; 128/206.27
(58) Field of Classification Search ............. 128/200.26, 128/201.26, 206.16, 206.27, 207.14; 600/194
See application file for complete search history.

(56) References Cited

U.S. PATENT DOCUMENTS

| | | | | |
|---|---|---|---|---|
| 5,178,132 A * | 1/1993 | Mahefky | ...................... | 600/194 |
| 5,845,634 A * | 12/1998 | Parker | ...................... | 128/200.26 |
| 5,850,832 A * | 12/1998 | Chu | ......................... | 128/200.26 |
| 6,427,686 B2 * | 8/2002 | Augustine et al. | ....... | 128/200.26 |
| 6,672,305 B2 * | 1/2004 | Parker | ...................... | 128/200.26 |
| 6,698,430 B2 * | 3/2004 | Van Landuyt | ........... | 128/207.15 |
| 2002/0112728 A1 * | 8/2002 | Landuyt | ................... | 128/207.15 |
| 2008/0146880 A1 * | 6/2008 | Malek | ........................... | 600/194 |

* cited by examiner

*Primary Examiner* — Lynne Anderson
(74) *Attorney, Agent, or Firm* — Alan Kamrath; Kamrath IP Lawfirm, PA

(57) ABSTRACT

The clip device is used for clipping a laryngeal mask airway. The laryngeal mask airway includes a gas filled portion and a tube portion. The clip device includes a first clip unit and a second clip unit. The second clip unit is connected to the first clip unit. The gas filled portion can be clipped between the first clip unit and the second clip unit.

13 Claims, 11 Drawing Sheets

LARYNGEAL MASK AIRWAY AND CLIP DEVICE

BACKGROUND OF THE INVENTION

1. Field of the Invention

The present invention relates to a medical instrument. More particularly, the present invention relates to a clip device for clipping a laryngeal mask airway and a laryngeal mask airway.

2. Description of the Related Art

In the case of anaesthesia or apnea patients, the top priority is the provision of pulmonary ventilation by emergency medical personnel. Among the various respiration sustaining instruments, the laryngeal mask airway (LMA), due to its ease of operability, is a common alternative to endotracheal intubation.

Please refer to FIG. 1 for the structure of a conventional LMA 10P. Basically, the LMA 10P comprises a flexible tubular portion 11P, an inflatable sealing cuff 13P, and an inflation tube 15P. The flexible tubular portion 11P comprises a first opening part 111P and a second opening part 112P. The inflatable sealing cuff 13P is disposed surrounding the first opening part 111P. The inflation tube 15P has one end connected to the inflatable sealing cuff 13P and the other end directing gas into the inflatable sealing cuff 13P.

Please refer to FIGS. 2 to 4 for illustrative diagrams showing the conventional laryngeal mask 10P in use. First, a user may insert the LMA 10P into a patient's mouth by the end having the inflatable sealing cuff 13P, which is in a deflated condition. When the inflatable sealing cuff 13P reaches a deeper part of the mouth, the user has to insert his/her finger into the patient's mouth to bend the front end of the LMA 10P to make the structure of the LMA 10P conform with the structure of the patient's upper jaw. In addition, due to the softness of the LMA 10P, the user may not exert force thereby. Thus, the user has to push aside the tongue with his/her finger to bend the first opening part 111P and the flexible tubular portion 11P to such an extent that they can reach past the upper jaw to the opening of the trachea, as shown in FIG. 3. In FIG. 4, it is shown that when the LMA 10P gets to a specific position, the user may then aerate the inflatable sealing cuff 13P from the inflation tube 15P so as to form a sealing mask in the patient's throat. The sealing mask may encompass the opening of the trachea and form an air passage thereby. After that, the user may direct gas, such as oxygen, from the second opening part 112P to maintain the patient's respiration.

Accordingly, during the installation of an LMA 10P, users always have to insert their finger(s) (especially their index fingers) into a patient's mouth to pass the soft, inconvenient LMA 10P through the upper jaw because of the obstruction caused by the patient's tongue. In general, this displacement of fingers may cause two problems. First, there is the risk that the user may be bitten by the patient during the installation of an LMA 10P. Second, in a case where a patient's oral space is overly small, which may be caused by an overly small mouth, an overly tight jaw joint, or an overly thick tongue, a user may encounter difficulty inserting his/her finger(s) into the patient's mouth, resulting in failure to install the LMA 10P.

Therefore, it is desirable to provide a clip device for clipping a laryngeal mask airway to mitigate and/or obviate the aforementioned problems.

SUMMARY OF THE INVENTION

It is an object of the present invention to provide a clip device for clipping a laryngeal mask airway.

It is another object of the present invention to provide a laryngeal mask airway for connecting to the clip device.

To achieve the aforementioned objects, the clip device of the present invention comprises a first clip unit and a second clip unit. The second clip unit is connected to the first clip unit. A gas filled portion of a laryngeal mask airway (LMA) can be clipped between the first clip unit and the second clip unit.

To achieve another aforementioned object, the LMA of the present invention comprises a tube portion, a gas filled portion and at least one protection cover. The tube portion comprises a first end and a second end. The gas filled portion is connected to the first end of the tube portion, and the gas filled portion comprises an upper side and a lower side. The at least one protection cover is connected to the gas filled portion, and the at least one protection cover is used for holding at least part of a main portion of the clip device.

According to one of the preferred embodiments of the present invention, the first clip unit is pivoted to the second clip unit, and a second main portion of the second clip unit is a U-shaped frame.

According to another embodiment of the present invention, the number of the at least one protection cover is two, and each of the protection covers respectively covers at least part of the upper side and at least part of the lower side.

Other objects, advantages, and novel features of the invention will become more apparent from the following detailed description when taken in conjunction with the accompanying drawings.

BRIEF DESCRIPTION OF THE DRAWINGS

These and other objects and advantages of the present invention will become apparent from the following description of the accompanying drawings, which disclose several embodiments of the present invention. It is to be understood that the drawings are to be used for purposes of illustration only, and not as a definition of the invention.

In the drawings, wherein similar reference numerals denote similar elements throughout the several views.

DETAILED DESCRIPTION OF THE PREFERRED EMBODIMENT

Figure 1:
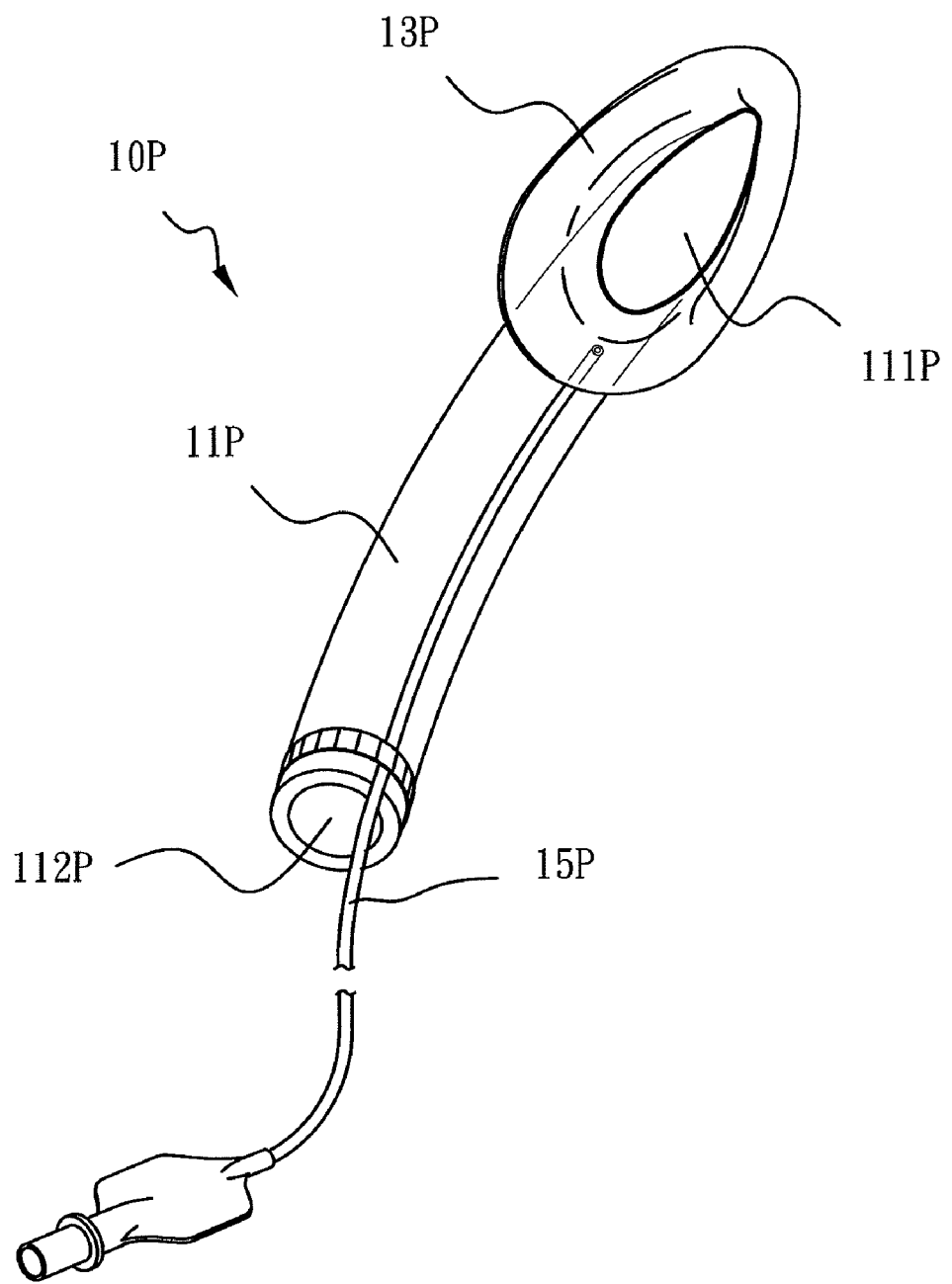
FIGS. 1 to 4 are illustrations of a laryngeal mask airway (LMA) used in the prior art.
Figure 2:
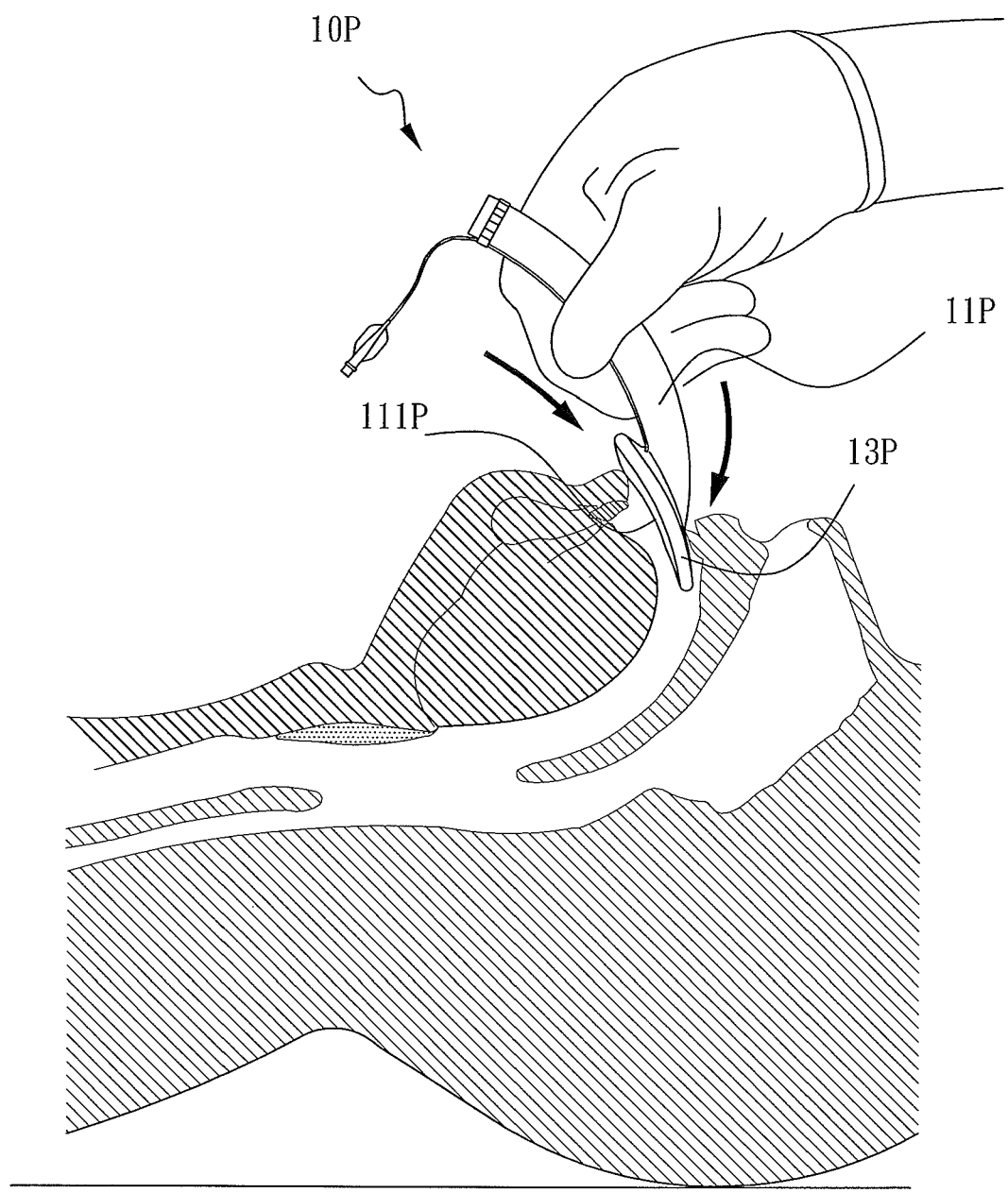
Figure 3:
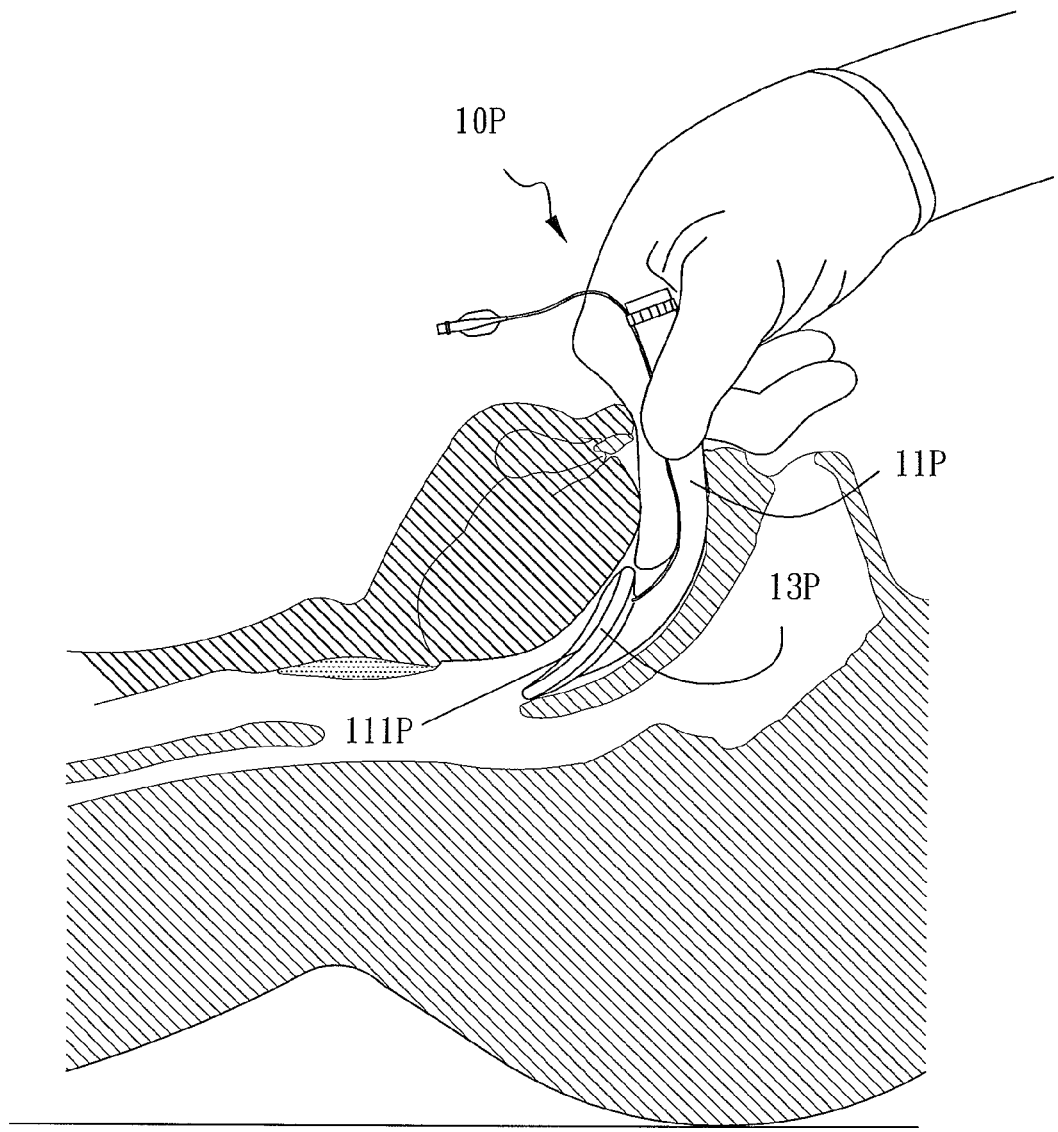
Figure 4:
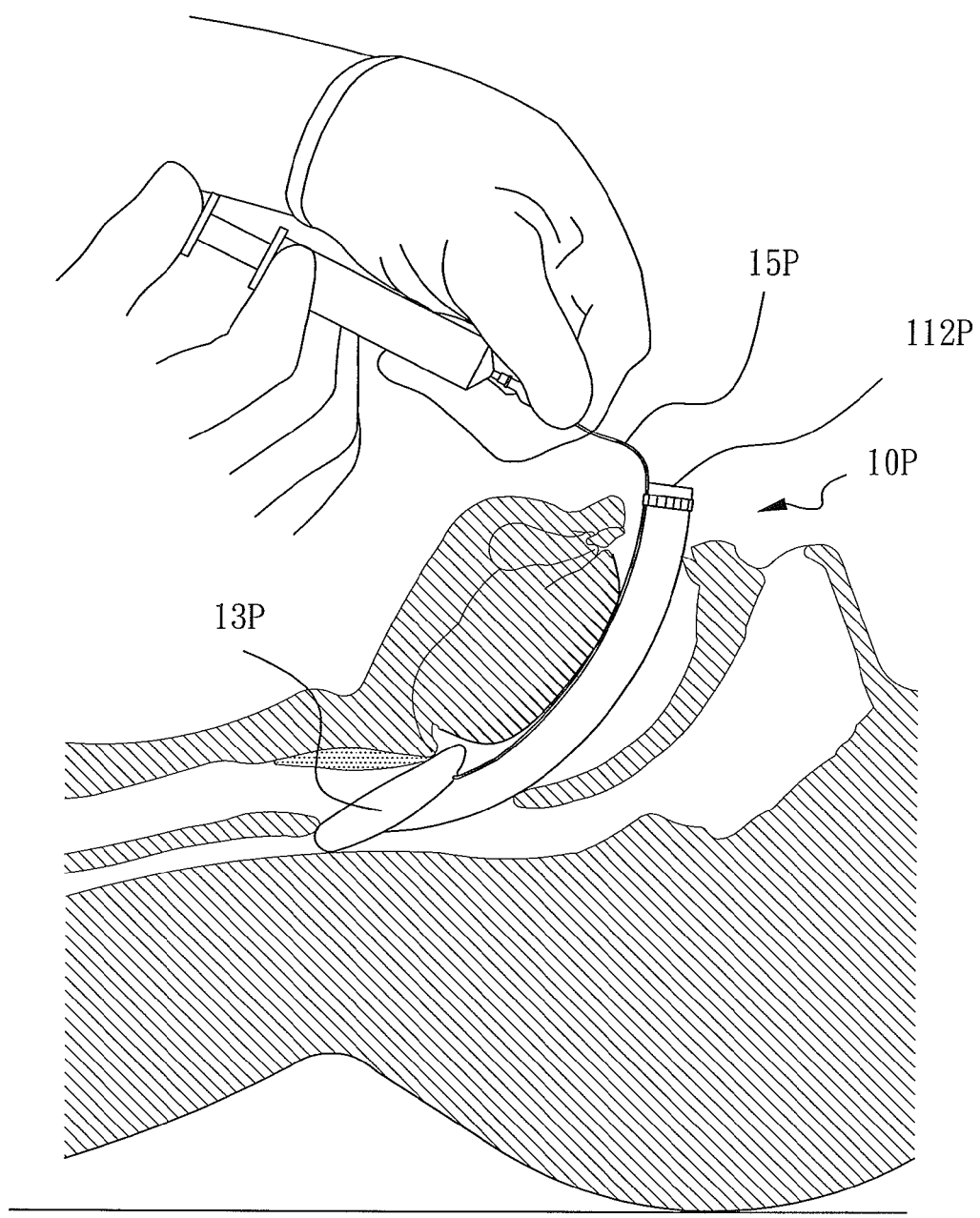
Figure 5:
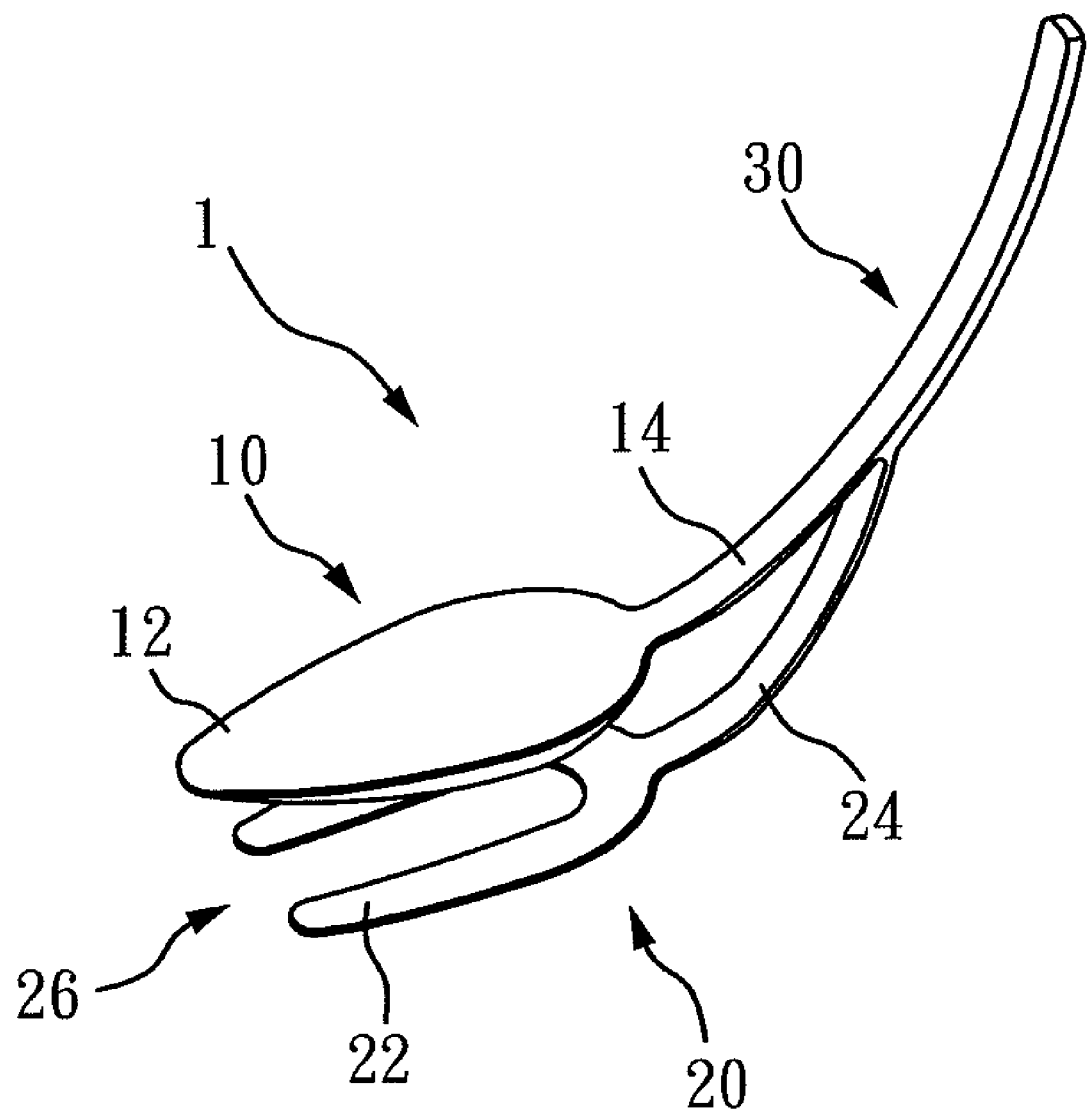
FIG. 5 is an illustration of a first embodiment of a clip device of the present invention.
Figure 6:
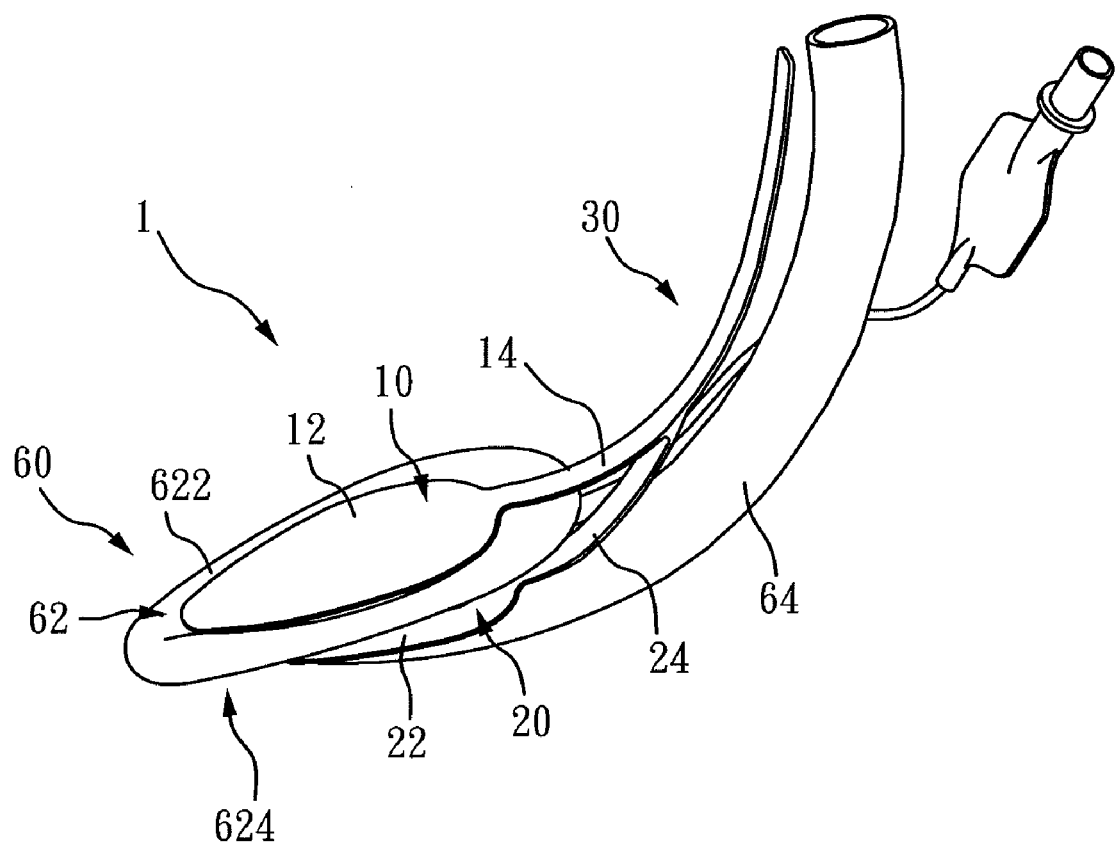
FIG. 6 is an illustration of the first embodiment of the clip device installed on an LMA of the present invention.

Please refer to both FIG. 5 and FIG. 6. FIG. 5 is an illustration of a first embodiment of a clip device 1 of the present invention. FIG. 6 is an illustration of the first embodiment of the clip device 1 installed on a laryngeal mask airway (LMA) 60 of the present invention. The clip device 1 of the present invention comprises a first clip unit 10 and a second clip unit 20. The second clip unit 20 is connected to the first clip unit 10. In this embodiment, the first clip unit 10 comprises a first main portion 12 and a first tail portion 14, and the second clip unit 20 comprises a second main portion 22 and a second tail portion 24.

When the clip device 1 is connected to the LMA 60, the clip device 1 could strengthen the structure of the LMA 60, such that the LMA 60 could smoothly slide into a patient's body, and slightly lift the patient's tongue by utilizing the first main portion 12 of the first clip unit 10.

The LMA 60 comprises a gas filled portion 62 and a tube portion 64. The gas filled portion 62 comprises an upper side 622 and a lower side 624. The gas filled portion 62 is connected to a first end 642 of the tube portion 64. The gas filled portion 62 is in the form of a circular hollow structure capable of storing gas therein. When the gas filled portion 62 is inflated with a predetermined volume of gas, the exterior of the gas filled portion 62 forms a soft surface. Since the LMA 60 is known as a prior art structure, there is no need for a more detailed description.

In this embodiment, the first main portion 12 is in the form of a curved surface. In order to match the shape of the gas filled portion 62 of the LMA 60, the shape of the first main portion 12 is egg-shaped (similar to the part of a spoon for spooning liquid), such that the periphery of the first main portion 12 could press the upper side 622 of the circular-shaped gas filled portion 62 (as shown in FIG. 6).

Please note that the first main portion of the clip device of the present invention could be in the form of other shapes. For example, the first main portion could be in the form of a plane or a frame (such as an O-shaped frame or a U-shaped frame). Furthermore, the shape of the first main portion could be oval-shaped or circular-shaped to match that of the gas filled portion 62.

In this embodiment, the second main portion 22 is a U-shaped frame in a fork shape, and the fork forms an opening 26. The opening 26 lies in the end of the second clip unit 20, and the width of the opening 26 is equal to or slightly greater than the external diameter of the tube portion 64. Thus, the tube portion 64 of the LMA 60 could be placed through the opening 26 for being mounted to the second main portion 22, and the periphery of the second main portion 22 could just press the lower side 624 of the circular-shaped gas filled portion 62. Please note that the second main portion 22 of the clip device 1 of the present invention could be a frame in the form of other shapes. For example, the second main portion 22 could be a C-shaped frame.

In this embodiment, at least part of the first tail portion 14 and the second tail portion 24 are combined with each other, thereby generating a fair holding force between the first tail portion 14 and the second tail portion 24. This holding force may vary according to the material of the first tail portion 14 and the second tail portion 24 and according to the combined proportion between first tail portion 14 and the second tail portion 24.

Please refer to FIG. 6. When the clip device 1 is connected to the LMA 60, the gas filled portion 62 is clipped between the first main portion 12 and the second main portion 22. At this time, the first tail portion 14 and the second tail portion 24 combined therewith form a handle portion 30, and the handle portion 30 is neighbor to the tube portion 64 of the LMA 60. More precisely, when a user (such as a doctor) operates the LMA 60 with the clip device 1 already connected thereto, he/she could hold the handle portion 30 and the tube portion 64 at the same time for an easy operation. In this embodiment, the handle portion 30 has a flexible characteristic, such that it could associate with the tube portion 64, which is also flexible.

Figure 7:
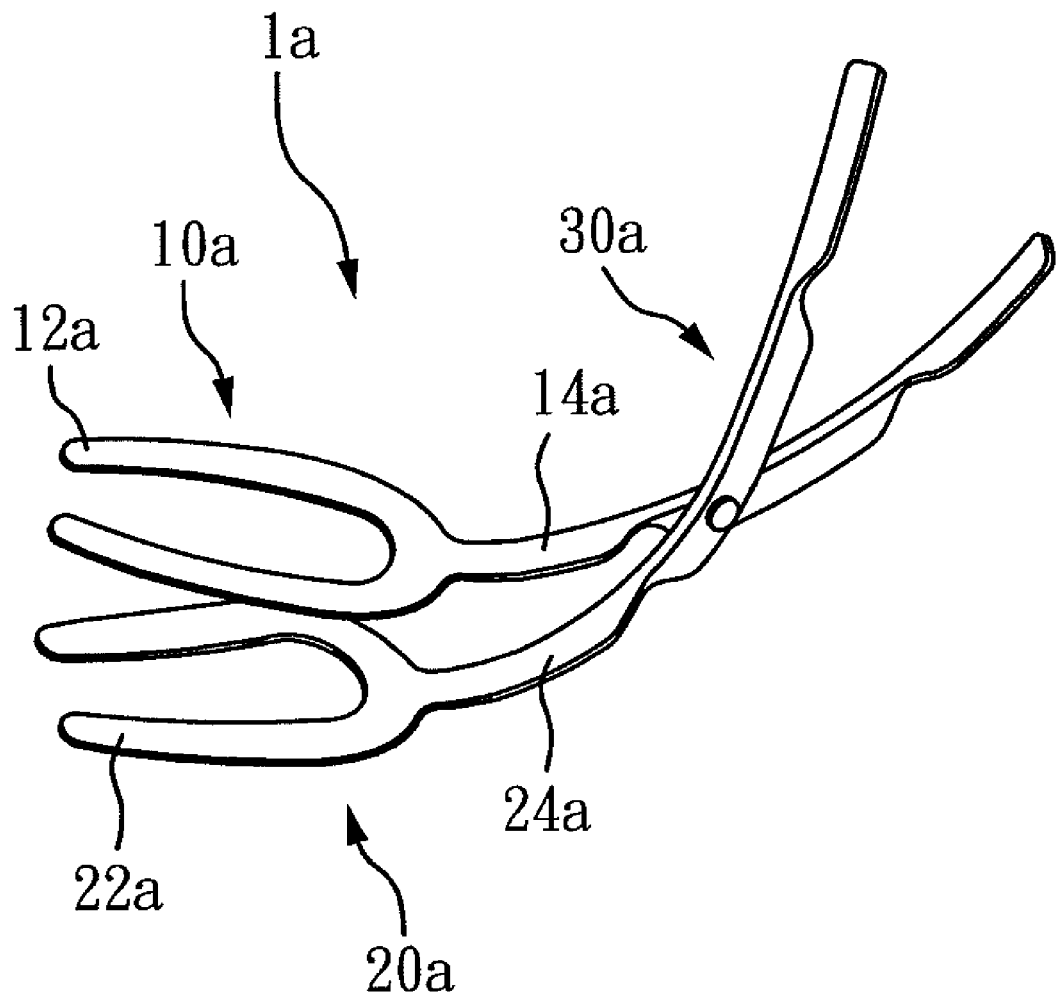
FIG. 7 is an illustration of a second embodiment of the clip device of the present invention.

Please refer to FIG. 7 for an illustration of a second embodiment of the clip device of the present invention. In this embodiment, the clip device 1a comprises a first clip unit 10a and a second clip unit 20a. The first clip unit 10a comprises a first main portion 12a and a first tail portion 14a, and the second clip unit 20a comprises a second main portion 22a and a second tail portion 24a.

The major difference between this and the above first embodiment is the way that the first clip unit and the second clip unit are connected. In this embodiment, the first clip unit 10a is pivoted to the second clip unit 20a. More precisely, the first tail portion 14a of the first clip unit 10a is pivoted to the second tail portion 24a of the second clip unit 20a. When the clip device 1a clips the LMA 60, the first tail portion 14a and the second tail portion 24a form a handle portion 30a for the user to hold. Please note that the pivot position of the first clip unit 10a and the second clip unit 20a is not limited to the above description.

Please also note that the structures and shapes of the first clip unit 10a and the second clip unit 20a are the same as those described in the above first embodiment. Specifically, they could be in the form of any shape (such as a frame, a plane, or a curved surface), and there is no need for a further detailed description.

Figure 8:
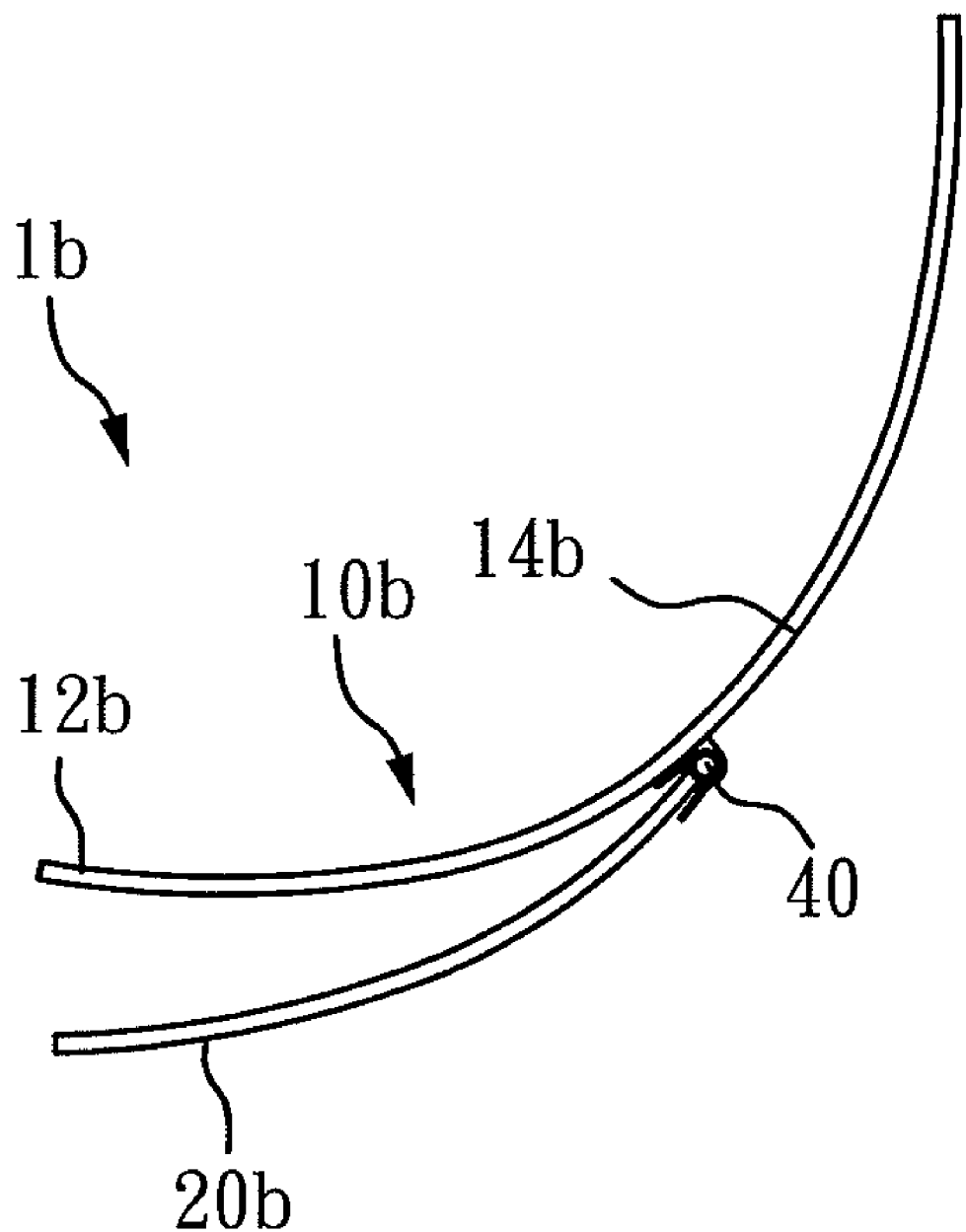
FIG. 8 is an illustration of a third embodiment of the clip device of the present invention.

Please refer to FIG. 8 for an illustration of a third embodiment of the clip device of the present invention. The difference between this and the second embodiment is the pivot position. In this embodiment, the clip device 1b comprises a first clip unit 10b and a second clip unit 20b. The first clip unit 10b comprises a first main portion 12b and a first tail portion 14b. One end of the second clip unit 20b is pivoted to the center of the first clip unit 10b. More precisely, one end of the second clip unit 20b is pivoted to the intersection of the first main portion 12b and the first tail portion 14b. This embodiment utilizes an elastic element 40 (such as a torsion spring) for pivoting, and provides force to the clip device 1b for clipping the gas filled portion 62 by using the elastic element 40. Please note that the position of the one end of the second clip unit 20b pivoted to the first clip unit 10b is not limited to the above description. For example, one end of the second clip unit 20b could also be pivoted to the first clip unit 10b or the first tail portion 14b.

Figure 9:
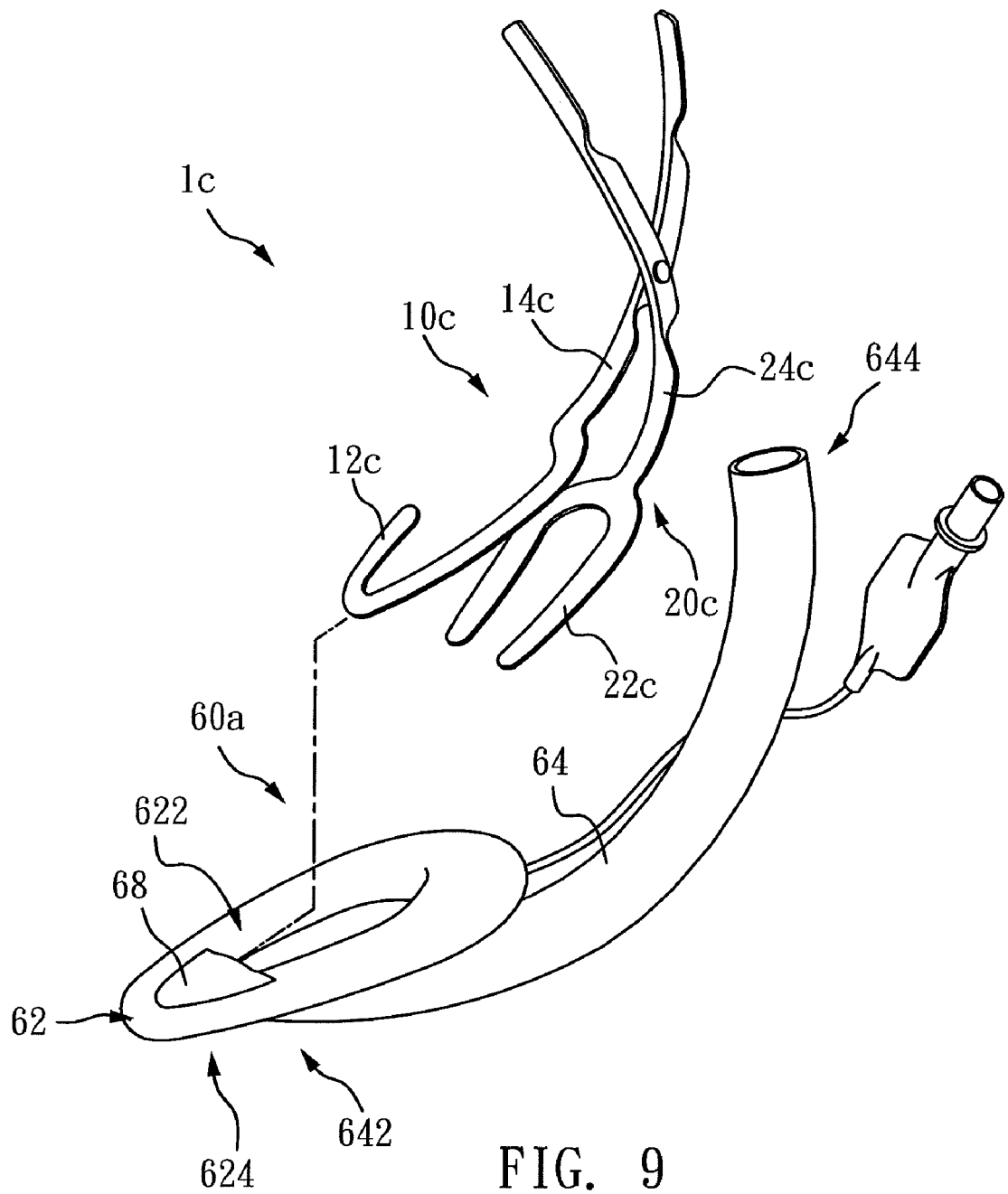
FIG. 9 is an exploded view of a fourth embodiment of the clip device and the LMA of the present invention.

Next, please refer to FIG. 9 for an exploded view of a fourth embodiment of the clip device and the LMA of the present invention. In this embodiment, the clip device 1c comprises a first clip unit 10c and a second clip unit 20c, and the first clip unit 10c is pivoted to the second clip unit 20c. The first clip unit 10c comprises a first main portion 12c and a first tail portion 14c, and the second clip unit 20c comprises a second main portion 22c and a second tail portion 24c. The difference between this and the above second embodiment is that the first main portion 12c of this embodiment is C-shaped, with a different opening position.

Please continue referring to FIG. 9 for the explanation of the LMA of the present invention. The LMA 60a comprises the gas filled portion 62, the tube portion 64 and a protection cover 68. The protection cover 68 is connected to the gas filled portion 62. The tube portion 64 comprises the first end 642 and a second end 644. The gas filled portion 62 is connected to the first end 642 of the tube portion 64, and the gas filled portion 62 comprises an upper side 622 and a lower side 624. In this embodiment, the protection cover 68 covers at least part of the upper side 622.

There are two purposes behind setting the protection cover 68: one is to prevent the first main portion 12c from directly contacting the throat and thus injuring the patient's tissue; and the other is to improve the operation when the user uses the clip device 1c.

There are two purposes behind setting the protection cover 68: one is to prevent the first main portion 12c from directly contacting the throat and thus injuring the patient's tissue; the other is to improve the operation when the user uses the clip device 1c.

Please note that the position and number of the protection cover 68 is not limited to the above description. For example, the protection cover (not shown in the figures) could also cover part of the lower side 624 and could also be used for holding part of the second main portion 22c. Alternatively, there could be two protection covers, with each respectively covering at least part of the upper side 622 and at least part of the lower side 624, as well as respectively used for holding part of the first main portion 12c and the second main portion 22c.

Figure 10:
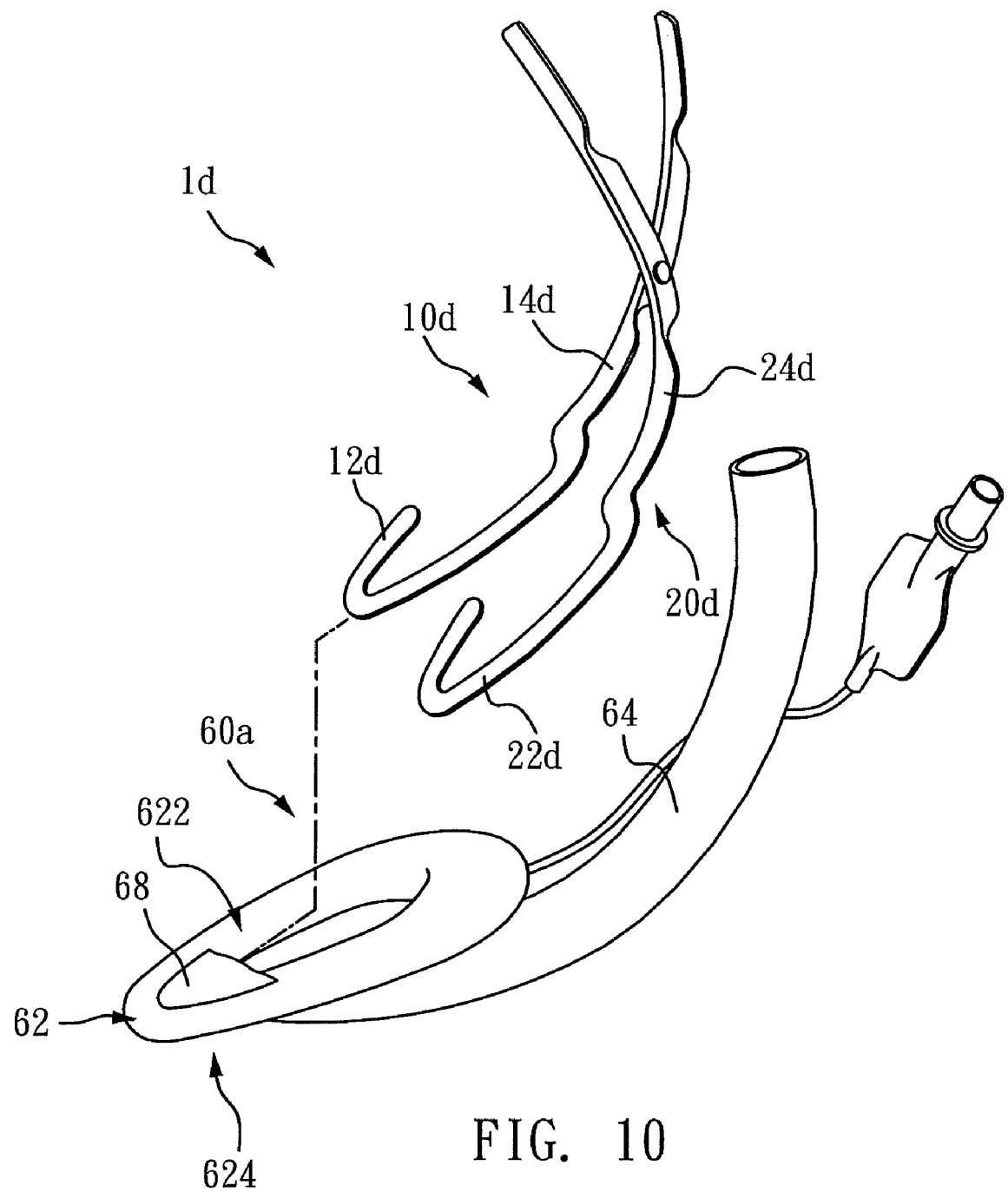
FIG. 10 is an exploded view of a fifth embodiment of the clip device and the LMA of the present invention.

Please refer to FIG. 10 for an exploded view of a fifth embodiment of the clip device and the LMA of the present invention. The clip device 1d comprises a first clip unit 10d and a second clip unit 20d. The first clip unit 10d is pivoted to the second clip unit 20d. The first clip unit 10d comprises a first main portion 12d and a first tail portion 14d, and the second clip unit 20d comprises a second main portion 22d and a second tail portion 24d. The difference between this and the above fourth embodiment is the shape of the second main portion 22d.

Figure 11:
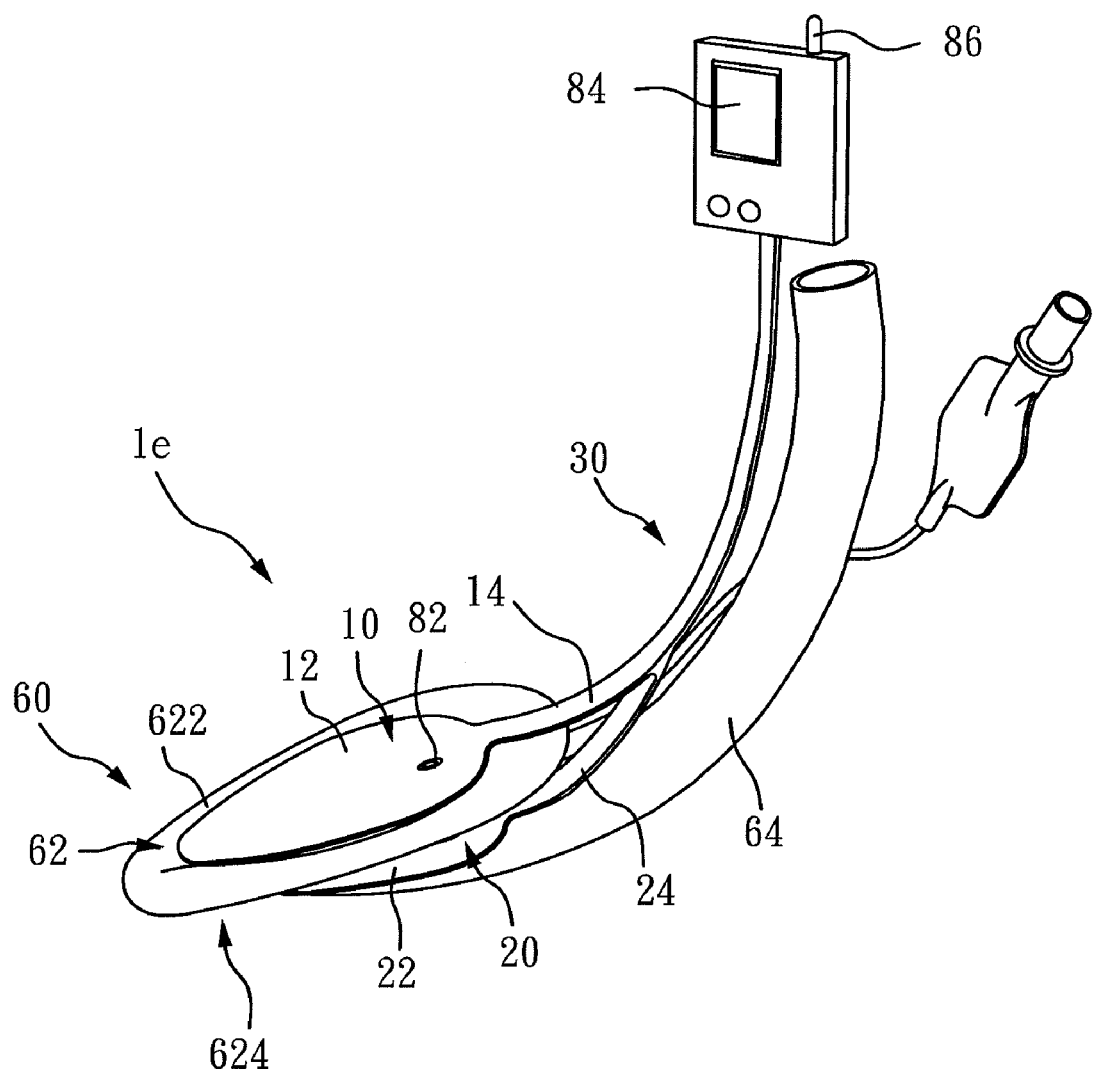
FIG. 11 is an illustration of a sixth embodiment of the clip device installed on the LMA of the present invention.

Please refer to FIG. 11 for an illustration of a sixth embodiment of the clip device installed on the LMA of the present invention. The major difference between this and the above embodiments is that the clip device 1e comprises an image-capturing unit 82, a display unit 84, and a signal emission unit 86. The image-capturing unit 82 is used for capturing an image from the patient's upper airway. The captured image may then be directly shown on the display unit 84 connected to the handle portion 30, such that the user could determine the position of the LMA in the patient's upper airway. In addition, the image captured by the image-capturing unit 82, depending on the user's need, could be transmitted to an external display (not shown in figures) via the signal emission unit 86. Therefore, the clip device 1e of the present invention not only provides a function of facilitating the user to clip the LMA 60 but also allows the user to conveniently observe the installation status so as to provide a more accurate status evaluation. Please note that the position of the image-capturing unit 82 is not limited to the above description.

Although the present invention has been explained in relation to its preferred embodiments, it is to be understood that many other possible modifications and variations can be made without departing from the spirit and scope of the invention as hereinafter claimed.

What is claimed is:

1. A clip device for clipping a laryngeal mask airway, the laryngeal mask airway comprising a gas filled portion and a tube portion, wherein the gas filled portion comprises an upper side and a lower side, the clip device comprising:
   a first clip unit comprising a first main portion and a first tail portion, wherein the first main portion presses the upper side; and
   a second clip unit connected to the first clip unit, with the gas filled portion being clipped between the first clip unit and the second clip unit, wherein the second clip unit comprises a second main portion and a second tail portion, and wherein the second main portion presses the lower side.

2. The clip device as claimed in claim 1, wherein the first tail portion and the second tail portion form a handle portion, and wherein the handle portion is neighbor to the tube portion.

3. The clip device as claimed in claim 1, wherein the first main portion is in the form of a curved surface or a plane.

4. The clip device as claimed in claim 1, wherein the first main portion is a frame.

5. The clip device as claimed in claim 1, wherein the shape of the first main portion is egg-shaped, oval-shaped, or circular-shaped.

6. The clip device as claimed in claim 5, wherein the first main portion is in a fork shape.

7. The clip device as claimed in claim 1, wherein the second main portion is a frame.

8. The clip device as claimed in claim 7, wherein the second main portion is C-shaped or U-shaped.

9. The clip device as claimed in claim 1, wherein the first clip unit is pivoted to the second clip unit.

10. The clip device as claimed in claim 1, wherein the first tail portion of the first clip unit is pivoted to the second clip unit.

11. The clip device as claimed in claim 1, wherein the first tail portion of the first clip unit is pivoted to the second tail portion of the second clip unit.

12. The clip device as claimed in claim 1, further comprising an image-capturing unit.

13. The clip device as claimed in claim 12, further comprising a display unit and a signal emission unit; wherein the display unit displays an image captured by the image-capturing unit, and wherein the signal emission unit transmits the image captured by the image-capturing unit to an external display.

* * * * *